(12) United States Patent
Fomitchov

(10) Patent No.: US 8,312,773 B2
(45) Date of Patent: Nov. 20, 2012

(54) LASER ULTRASONIC DEVICE

(75) Inventor: Pavel Alexeyevich Fomitchov, New York, NY (US)

(73) Assignee: General Electric Company, Niskayuna, NY (US)

( * ) Notice: Subject to any disclaimer, the term of this patent is extended or adjusted under 35 U.S.C. 154(b) by 910 days.

(21) Appl. No.: 12/337,664

(22) Filed: Dec. 18, 2008

(65) Prior Publication Data
US 2010/0154549 A1 Jun. 24, 2010

(51) Int. Cl.
*G01N 29/04* (2006.01)
(52) U.S. Cl. .......................... 73/643; 73/655
(58) Field of Classification Search .............. 73/643, 73/596, 627, 628, 653, 655; 385/115, 119; 356/73.1
See application file for complete search history.

(56) References Cited

U.S. PATENT DOCUMENTS

| | | | |
|---|---|---|---|
| 4,953,932 A * | 9/1990 | Mihich | 385/26 |
| 5,329,354 A * | 7/1994 | Yamamoto et al. | 356/490 |
| 5,457,997 A | 10/1995 | Naruo et al. | |
| 5,684,592 A | 11/1997 | Mitchell et al. | |
| 6,008,887 A * | 12/1999 | Klein et al. | 356/28.5 |
| 6,747,268 B1 * | 6/2004 | Ume | 250/227.11 |
| 7,369,250 B2 | 5/2008 | Dubois et al. | |
| 7,983,520 B2 * | 7/2011 | Bringuier et al. | 385/100 |
| 2001/0039836 A1 | 11/2001 | Ogawa | |
| 2007/0187632 A1 * | 8/2007 | Igarashi | 250/559.36 |
| 2010/0206082 A1 * | 8/2010 | Shimazaki et al. | 73/627 |

FOREIGN PATENT DOCUMENTS

JP 363218827 * 9/1988

OTHER PUBLICATIONS

B. A., William and R. J., Dewhurst (1996)'A Fibre-Optic Detection System for Laser-Ultrasound Lamb-Wave Examination of Defects in Thin Materials',Nondestructive Testing and Evaluation,12:6,343-353; Retrieved from the internet: <URL: http://dx.doi.org/10.1080/10589759608952858>.

* cited by examiner

*Primary Examiner* — J M Saint Surin
(74) *Attorney, Agent, or Firm* — Seema Katragadda

(57) ABSTRACT

A laser ultrasonic device is disclosed. The laser ultrasonic device comprises an ultrasonic generation system capable of generating ultrasonic waves on a surface of a sample, said system comprising a first collection of optical fiber output ends arranged in a first pattern.

36 Claims, 6 Drawing Sheets

LASER ULTRASONIC DEVICE

BACKGROUND

The invention relates generally to ultrasonic devices, and more specifically to laser ultrasonic devices.

Laser-ultrasonic devices use lasers to generate and detect ultrasonic waves within solid samples. Techniques based on such laser ultrasonic devices are non-contact techniques, and are useful to measure a variety of material properties, such as the presence of defects. The basic components of a laser ultrasonic device are an ultrasonic generation system and an ultrasonic detection system.

The ultrasonic generation system usually consists of a high power generation laser capable of producing short pulses (typically of duration lying between femtoseconds to tens of nanoseconds) of laser energy. Many currently used generation lasers are solid state Q-Switched Nd:YAG and gas lasers (carbon dioxide or Excimers).

One known laser based ultrasonic generation technique utilizes the principle of thermoelastic expansion. Specifically, ultrasonic waves are generated on the surface or within the bulk of a sample by a sudden thermal expansion due to a sudden heating of a small surface of the sample material by the pulse of laser energy from the generation laser. Another known laser based ultrasonic generation technique is based on laser ablation of a sample.

Known ultrasonic detection systems usually include a detection laser, used to provide an interrogating beam of laser energy, and an interferometry based detection scheme. Typically, a detection laser provides continuous or long pulses (typically of a duration up to tens of microseconds) of laser energy and with long coherence length. The interrogating beam is scattered by the sample surface, wherein the sample surface is perturbed by an arrival of ultrasonic waves. The interferometry based detection scheme is then used to detect this perturbation.

A laser ultrasonic system that has a high signal-to-noise ratio, is compact enough to enable detection of flaws or defects in otherwise difficult to access locations, and is economical to construct and maintain is highly desirable.

BRIEF DESCRIPTION

Embodiments of the invention are directed towards a laser ultrasonic device.

A laser ultrasonic device, comprising an ultrasonic generation system capable of generating ultrasonic waves on a surface of a sample, said system comprising a first collection of optical fiber output ends arranged in a first pattern.

A laser ultrasonic device, comprising an ultrasonic generation system capable of generating ultrasonic waves on a surface of a sample, said ultrasonic generation system comprising a first collection of optical fiber output ends arranged in a first pattern, and an ultrasonic detection system capable of detecting ultrasonic waves on the surface of a sample, said ultrasonic detection system comprising a second collection of optical fiber output ends arranged in a second pattern, and a third collection of optical fiber input ends arranged in a third pattern.

A laser ultrasonic device, comprising an ultrasonic generation system capable of generating ultrasonic waves within a bulk of a sample, said ultrasonic generation system comprising a first collection of optical fiber output ends arranged in a first pattern, and an ultrasonic detection system capable of detecting ultrasonic waves within the bulk of the sample, said ultrasonic detection system comprising a second collection of optical fiber output ends arranged in a second pattern, a third collection of optical fiber input ends arranged in a third pattern.

These and other advantages and features will be more readily understood from the following detailed description of preferred embodiments of the invention that is provided in connection with the accompanying drawings.

DRAWINGS

DETAILED DESCRIPTION

In the following description, whenever a particular aspect or feature of an embodiment of the invention is said to comprise or consist of at least one element of a group and combinations thereof, it is understood that the aspect or feature may comprise or consist of any of the elements of the group, either individually or in combination with any of the other elements of that group.

In the following specification and the claims that follow, the singular forms "a," "an," and "the" include plural referents unless the context clearly dictates otherwise.

Approximating language, as used herein throughout the specification and claims, may be applied to modify any quantitative representation that could permissibly vary without resulting in a change in the basic function to which it is related. Accordingly, a value modified by a term or terms, such as "about" or "substantially," may be not to be limited to the precise value specified, and may include values that differ from the specified value. In at least some instances, the approximating language may correspond to the precision of an instrument for measuring the value.

As used herein, the term "within," when used in context of discussion of any physical entity may refer to a bulk of the physical entity or it may refer to a surface of the physical entity, or it may refer to both the bulk and the surface of the physical entity.

In the present discussions it is to be understood that, unless explicitly stated otherwise, any range of numbers stated during a discussion of any region within, or physical characteristic of, a semiconductor device, is inclusive of stated end points of the range.

As used herein, the term "adjacent," when used in context of discussion of different parts comprising the laser ultrasonic device may refer to the situation where the parts under discussion are immediately next to each other, or it may also refer to a situation wherein intervening parts are present between the parts under discussion.

As used herein, the term "communication," when used in context of discussion of at least two parts of the laser ultrasonic device means that any change in an electrical characteristic of one part is detectable and measurable via, the other part.

As used herein, the phrase "region of interest," when used in the context of discussion of any possible application of a laser ultrasonic device refers to a spatial region, wherein the spatial region may be an area or a volume where it is desired to induce and propagate ultrasonic waves. The ultrasonic waves propagate though the region of interest, and from a measurement and analysis of these ultrasonic waves, one may be able to extract information about features, such as defects or flaws, that are present within the region of interest.

Figure 1:
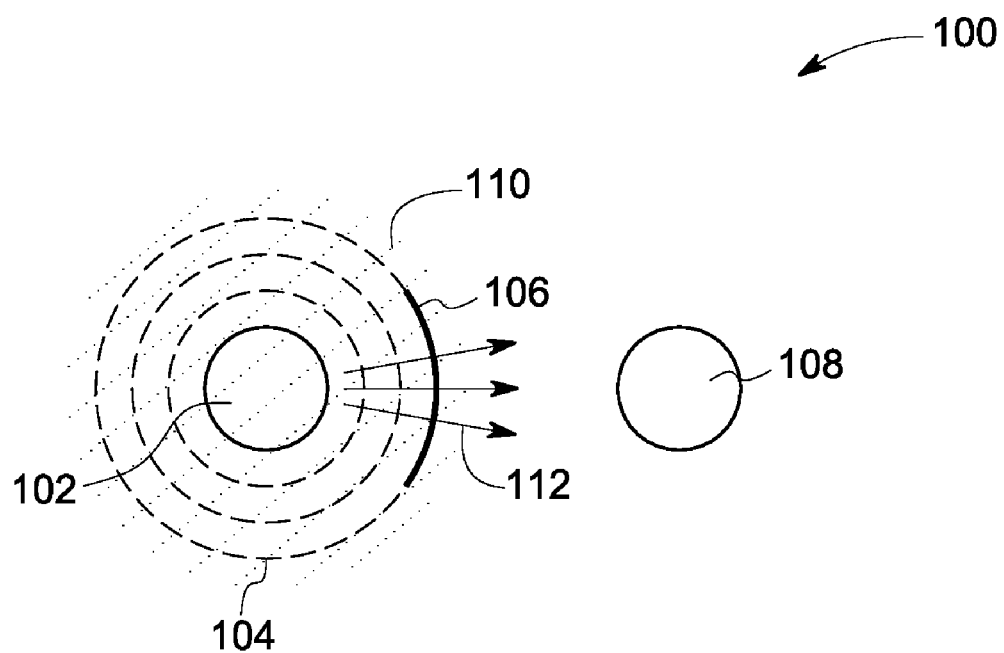
FIG. 1 is a schematic view of a generation center of ultrasonic wave flux produced via a typical prior art laser ultrasonic device.

With specific reference to FIG. 1, there is shown in schematic view 100, a generation center 102 of ultrasonic wave flux 104. The generation center 102 is typical of generation centers produced via a typical prior art laser ultrasonic device that includes an ultrasonic wave generation laser (not shown). Depending on the properties of a medium 110 through which the ultrasonic wave flux 104 is propagating, the ultrasonic wave flux 104 propagates substantially outwards in all spatial directions 112 from the generation center 102. It may be evident that, only a portion 106 of the total ultrasonic wave flux 104 travels substantially towards an ultrasonic wave flux detection probe 108. As shown in FIG. 1, the ultrasonic waves produced via conventional laser ultrasonic devices have little or no directivity as they travel away from a generation center 102. Furthermore, conventional ultrasonic wave flux detection probes of type 108 have poor directional sensitivity towards ultrasonic wave flux 104, that is, conventional ultrasonic wave flux detection probes have little or no ability to distinguish between ultrasonic wave flux traveling along a given direction from that along any other direction. In typical laser ultrasonic prior art devices, a collection efficiency of the ultrasonic wave flux probe 108 (ratio of a signal contained within the ultrasonic wave flux 106 to a signal contained within the total ultrasonic wave flux 104) is typically less than approximately 0.5%. It is known in the art that a signal to noise ratio capability of an ultrasonic wave flux probe is a direct function of the collection efficiency of the ultrasonic wave flux probe.

Conventional techniques of enhancing the signal-to-noise ratio of an ultrasonic wave flux detection probe 108 have included incorporation of optical systems (not shown). As is known in the art, it is typically possible to achieve collection efficiency of approximately 0.5% via the incorporation of such optical systems. However, as is known in the art, such optical systems are bulky and large in size. For instance, as is known in the art, the footprint of a typical optical system is about 5 centimeters to about 13 centimeters. Consequently, the utility of such laser ultrasonic devices that include such optical systems, for applications where a region of interest is placed in-situ, may be severely compromised. For instance, in typical steam turbines, a cross-sectional area of access points for in-situ measurements is smaller than about 5 cm². It is clear that, conventional laser ultrasonic devices including optical systems, of the type discussed above, will be of only limited utility for measurements on such devices.

A laser ultrasonic device, that displays an enhanced signal-to-noise ratio, and is yet compact enough to be useful for in-situ applications of the type discussed above for example, would therefore be highly desirable.

Figure 3:
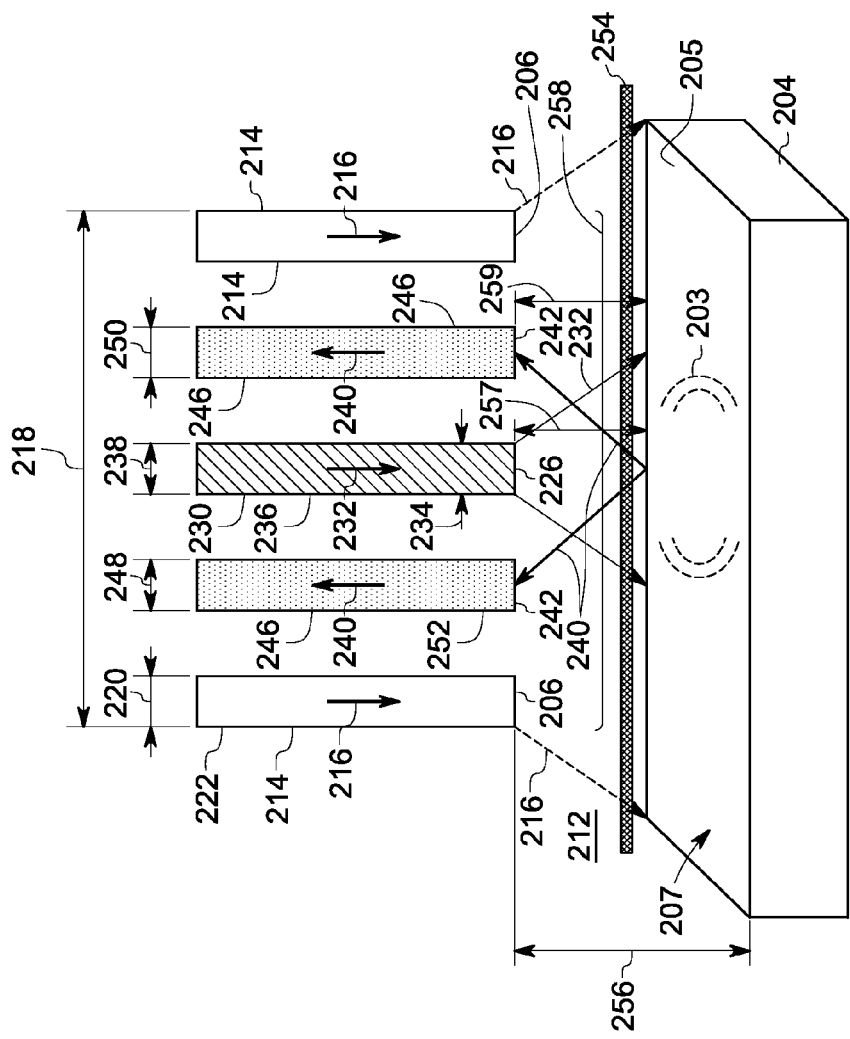
FIG. 3 is a schematic side view of the laser ultrasonic device of FIG. 2, in accordance with one embodiment of the invention.
Figure 2:
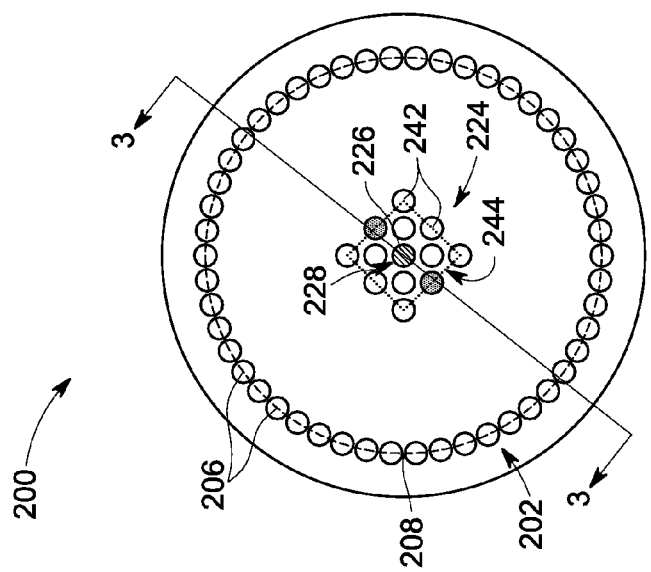
FIG. 2 is a cross-sectional view of a laser ultrasonic device in accordance with one embodiment of the invention.

With specific reference to FIGS. 2 and 3, in accordance with one embodiment of the invention, a cross-sectional view of a laser ultrasonic device 200 including an ultrasonic generation system 202 capable of generating ultrasonic waves 203 on a surface 205 of a sample 204 is shown. The ultrasonic generation system 202 includes a first collection of optical fiber output ends 206 arranged in a first pattern 208. In the non-limiting example shown in FIG. 2, the first pattern 208 is substantially a circle. However, it is to be clearly understood that the shape of first pattern 208 is dependent on several factors such as the type of sample 204, the strength of ultrasonic waves needed to be introduced within the sample 204, the medium 212 between ultrasonic generation system and the sample 204, amongst other factors. For instance, in other embodiments, the first pattern 208 can be a line, a point, a line, an arc, a square, a rectangle, or any combinations thereof. In one embodiment of the invention, the first pattern 208 comprises a symmetrical pattern, or combinations of symmetrical patterns.

In accordance with one embodiment of the invention, FIG. 3 depicts a side view along 3-3 (FIG. 2) of a first collection of optical fibers 214 corresponding to the first collection of optical fiber ends 206. The first collection of optical fibers 214 is capable of guiding a first light flux 216 for delivery to a desired location 207 on the surface 205 of the sample 204. Delivery of the first light flux 216 to location 207 on the surface 205 of sample 204, via the first collection of optical fiber output ends 206, likely results in a local thermoelastic heating of the location 207 and its vicinity. As a result of the local thermoelastic heating, ultrasonic waves 203 are produced at location 207, that is, location 207 acts as a generation center for ultrasonic waves 203. The ultrasonic waves propagate along the surface 205 of the sample 204. The amount of thermoelastic heating, of location 207 on surface 205 of sample 204 depends, among other factors, on an intensity of the first light flux 216 that is incident at location 207. Therefore, in one embodiment of the invention, an intensity of the first light flux 216 may be chosen to lie within a range sufficient for generation of ultrasonic waves in thermoelastic mode. In one embodiment of the invention, an intensity of the first light flux 216 may be chosen to lie within a range sufficient for generation of ultrasonic waves in laser ablation mode.

For a given size of location 207, the intensity of the first light flux 216 is a function of the energy contained within the first light flux 216, which in turn is a function of electromagnetic energy that contained within the first light flux 216. In one embodiment of the invention, the first light flux 216 includes electromagnetic energy having a wavelength within a range from about 0.2 micrometers to about 15 micrometers. In one embodiment of the invention, the first light flux 216 includes electromagnetic energy having a wavelength within a range from about 0.3 micrometers to about 1.5 micrometers. In one embodiment of the invention, the first light flux 216 includes electromagnetic energy having wavelength within a range from about 4 micrometers to about 11 micrometers.

Without being limited by any particular theory, transmission characteristics, such as transmission loss of electromagnetic energy of a given wavelength through any individual optical fiber 222, are a function of a core diameter 220 of the individual optical fiber 222. In one embodiment of the invention, a core diameter 220 of individual optical fibers 222 corresponding to the first collection of optical fiber output ends 206 independently lies within a range from about 5 micrometers to about 1000 micrometers. In one embodiment of the invention, a core diameter 220 of individual optical fibers 222 corresponding to the first collection of optical fiber output ends 206 independently lies within a range from about 50 micrometers to about 300 micrometers.

The efficient generation of ultrasonic waves 203 on the surface 205 is dependent on several, potentially interrelated, factors. The size of the location 207, and a distance 256 between the ultrasonic generation system 202 and the surface 205 of sample 204, are two such factors that are interrelated via, for example, the numerical aperture of the individual optical fibers 222 corresponding to the first collection of optical fibers 214. In one embodiment of the invention, a numerical aperture of individual optical fibers 222 corresponding to the first collection of optical fiber output ends 206 independently lies within a range from about 0.05 to about 0.6. In one embodiment of the invention, a numerical aperture of individual optical fibers 222 corresponding to the first collection of optical fibers output ends 206 independently lies within a range from about 0.05 to about 0.25.

Typical applications require the production of ultrasonic waves at locations within a system that are otherwise (without disassembling the system) accessible only via access points that typically have a cross-sectional area of less than about 5 cm². Applications such as these, where ultrasonic waves need to be generated "in-situ," would therefore benefit by having an ultrasonic generation system 202 that is capable to accessing such location via the available access points. Therefore, in one embodiment of the invention, a cross-sectional area 218 of the first collection of optical fibers 214 is within a range from about 0.1 cm² to about 200 cm². In one embodiment of the invention, a cross-sectional area 218 of the first collection of optical fibers 214 is within a range from about 0.2 cm² to about 10 cm².

In one embodiment of the invention, the laser ultrasonic device 200 further includes an ultrasonic detection system 224 capable of detecting ultrasonic waves 203 on the surface 205 of the sample 204. The ultrasonic detection system 224 includes a second collection of optical fiber output ends 226 arranged in a second pattern 228. In the example shown in FIG. 2, the second pattern 228 is substantially a point. However, it is to be clearly understood that the shape of second pattern 228 is dependent on several factors such as the type of sample 204, the strength of ultrasonic waves that need to be detected within the sample 204, the medium 212 between ultrasonic generation system and the sample 204, amongst other factors. For instance, in other embodiments, the second pattern 228 can be a line, a circle, an arc, a square, a rectangle, or any combinations thereof. In one embodiment of the invention, the first pattern 228 comprises a symmetrical pattern, or combinations of symmetrical patterns.

In accordance with one embodiment of the invention, a second collection of optical fibers 230 corresponding to the second collection of optical fiber output ends 226 is capable of guiding a second light flux 232. The second light flux 232 interrogates the surface 205 of sample 204 on which are propagating ultrasonic waves 203. The efficiency of interrogation is a function, amongst other factors, of the intensity of the second light flux 232. An intensity of the second light flux 232 may be chosen so that, a portion of a third light flux 240 (discussed below) that is collected by the ultrasonic detection system 224 is sufficient to enable the ultrasonic detection system 224 to operate in a shot noise limited regime.

Without being limited to any particular theory, the signal-to-noise ratio, of the ultrasonic detection system 224, for a given sample 204 having specific properties, and for a given set of ultrasonic waves 203 having specific properties, is a function of a wavelength of electromagnetic energy contained within the second light flux 232. The specific properties of the sample 204 that are potentially relevant include, but are not limited to, anisotropy and density. The specific properties of the ultrasonic waves 203 that are potentially relevant include, but are not limited to, amplitude and frequency. In one embodiment of the invention, the second light flux 232 includes electromagnetic energy having a wavelength within a range from about 0.2 micrometers to about 15 micrometers. In one embodiment of the invention, the first light flux 232 includes electromagnetic energy having wavelength within a range from about 0.4 micrometers to about 1.5 micrometers.

Without being limited by any particular theory, transmission characteristics such as transmission loss of electromagnetic energy of a given wavelength through any individual optical fiber 236 are a function of a core diameter 234 of the optical fiber individual optical fiber 236. In one embodiment of the invention, a core diameter 234 of individual optical fibers 236 corresponding to the second collection of optical fiber output ends 226 independently lies within a range from about 0.03 micrometers to about 1000 micrometers. In one embodiment of the invention, a core diameter 234 of individual optical fibers 226 corresponding to the second collection of optical fiber output ends 226 independently lies within a range from about 50 micrometers to about 500 micrometers.

The efficient interrogation of ultrasonic waves 203 on the surface 205 is dependent on several, potentially interrelated factors. The size ("footprint") of the second light flux where it interrogates ultrasonic waves 203 on the surface 205 of the sample 204, and the distance 257 between the ultrasonic detection system 224 and the surface 205 of sample 204, are two such factors, that are interrelated via, for example, the numerical aperture of the individual optical fibers 236 corresponding to the second collection of optical fiber output ends 226. In one embodiment of the invention, a numerical aperture of individual optical fibers 236 corresponding to the second collection of optical fiber output ends 226 independently lies within a range from about 0.05 to about 0.6. In one embodiment of the invention, a numerical aperture of individual optical fibers 236 corresponding to the second collection of optical fiber 226 output ends independently lies within a range from about 0.1 to about 0.4.

As discussed herein, typical applications require the detection of ultrasonic waves at locations within a system that are otherwise (without disassembling the system) accessible only via access points that typically have a cross-sectional area of less than about 5 cm². Applications such these, where ultrasonic waves need to be detected "in-situ," would therefore benefit by having an ultrasonic detection system 224 that is capable to accessing such location via the available access points. Therefore, in one embodiment of the invention therefore, a cross-sectional area 238 of the second collection of optical fibers 230 is within a range from about 0.1 cm² to about 5 cm². In one embodiment of the invention, a cross-sectional area 238 of the second collection of optical fibers 230 is within a range from about 0.2 cm² to about 1 cm².

In one embodiment of the invention, the first light flux 216 and the second light flux 232 independently include a laser beam. The laser beam may be produced, for example using any suitable laser generation system (not shown). An arrangement of the input ends of the first collection of optical fibers 214, and an arrangement of input ends of the second collection of optical fibers 230 can independently be enclosed within a mechanical coupling device (not shown) that has a round coupling end (not shown). It is likely that the round coupling end would aid in an enhanced coupling efficiency of light flux delivery between the laser generation system and the corresponding collection of optical fibers. Furthermore, the coupling may serve to hold the arrangement of the input ends of the first collection of optical fibers 214 in a pattern that aids the first light flux 216 to generate ultrasonic waves 203 on the surface 205 of sample 204 that have, for example, a plain wavefront or a focused wavefront. In accordance with one embodiment of the invention, the second light flux 232 is made to scatter off the surface 205 of the sample 204 to form a third light flux 240. In one embodiment, the third light flux 240 includes a non-imaging light beam.

In accordance with one embodiment of the invention, the ultrasonic detection system 224 further includes a third collection of optical fiber input ends 242 arranged in a third pattern 244. In the example shown in FIG. 2, the third pattern 244 is substantially a circle. However, it is to be clearly understood that the shape of third pattern 244 is dependent on several factors such as the type of sample 204, the strength of ultrasonic waves 203 that required to be detected on the surface 205 of the sample 204, the medium 212 between ultrasonic detection system 224 and the sample 204, amongst other factors. For instance, in other embodiments, the third pattern 244 can be a point, a line, an arc, a square, a rectangle, or any combinations thereof. In one embodiment of the invention, the third pattern 244 includes a symmetrical pattern, or combinations of symmetrical patterns.

In accordance with one embodiment of the invention, the third collection of optical fibers input ends 242 is capable of collecting at least a portion of the third light flux 240. The portion of the third light flux 240 may now be delivered, via a third collection of optical fibers 246 corresponding to the third collection of optical fiber input ends 242 to a suitable optical ultrasonic detector (not shown). Non-limiting examples of optical ultrasonic detectors include a Fabry-Perot interferometer, and photorefractive interferometer.

In accordance with one embodiment of the invention, a third collection of optical fibers 246 corresponding to the third collection of optical fiber input ends 242 is capable of guiding at least a portion of the third light flux 240. Without being limited to any particular theory, transmission characteristics such as transmission loss of electromagnetic energy of a given wavelength through any individual optical fiber 252 are a function of a core diameter 250 of the individual optical fibers 252. In one embodiment of the invention, a core diameter 250 of individual optical fibers 252 corresponding to the third collection of optical fiber input ends 242 independently lies within a range from about 0.05 micrometers to about 1000 micrometers. In one embodiment of the invention, a core diameter 250 of individual optical fibers 252 corresponding to the third collection of optical fiber input ends 242 independently lies within a range from about 50 micrometers to about 300 micrometers.

The efficient collection of the third light flux 240, by the third collection of optical fiber input ends 242, is dependent on several, potentially interrelated, factors. The cross-sectional area over which the third collection of optical fiber input ends 242 are able to collect the third light flux 240, and a distance 259 between the ultrasonic detection system 224 and the surface 205 of sample 204, are two such factors that are interrelated via, for example, the numerical aperture of the individual optical fibers 222 corresponding to the first collection of optical fibers 214. In one embodiment of the invention therefore, a numerical aperture of individual optical fibers 246 corresponding to the third collection of optical fiber input ends 242 independently lies within a range from about 0.05 to about 0.6. In one embodiment of the invention, a numerical aperture of individual optical fibers 246 corresponding to the third collection of optical fiber input ends 242 independently lies within a range from about 0.1 to about 0.3. In one embodiment of the invention, a numerical aperture of individual optical fibers 246 corresponding to the third collection of optical fiber input ends 242 independently lies within a range from about 0.3 to about 0.6.

As discussed herein, typical applications require the detection of ultrasonic waves at locations within a system that are otherwise (without disassembling the system) accessible only via access points that typically have a cross-sectional area of less than about 5 cm$^2$. Applications such these, where ultrasonic waves need to be detected "in-situ," would therefore benefit by having an ultrasonic detection system 224 that is capable to accessing such locations via the available access points. Therefore, in one embodiment of the invention, a cross-sectional area 248 of the third collection of optical fibers 246 is within a range from about 0.1 cm$^2$ to about 5 cm$^2$. In one embodiment of the invention, a cross-sectional area 248 of the third collection of optical fibers 246 is within a range from about 0.1 cm$^2$ to about 10 cm$^2$.

As discussed herein, the laser ultrasonic system 200 incorporates collections of optical fibers for both generation and detection of ultrasonic waves. For instance, the ultrasonic generation system 202 includes the first collection of optical fibers 214, and the ultrasonic detection system 224 includes the second collection of optical fibers 230 and the third collection of optical fibers 246. The first pattern 208 and the second pattern 228 aid in fashioning respectively the first light flux 216, and second light flux 232 into non-imaging light beams that are then used to create required illumination patterns on the surface 205 of sample 204, such as for instance at location 207. The illumination pattern created by the first light flux 216 is used to generate the ultrasonic waves 203 on the surface 205. The illumination pattern created by the second light flux 232 is used to interrogate the surface 205 for ultrasonic waves 203. It may be evident from FIG. 2 that the arrangement of the first collection of optical fiber output ends 206 allows one control over the directivity of generated ultrasound waves 203. It may also be evident from FIG. 2 that the arrangement of the second collection of optical fiber output ends 226, and the arrangement of the second collection of optical fiber input ends 242, allows one control over the directional sensitivity of detection of the generated ultrasound waves 203.

At the sample end of the laser ultrasonic generation system 200, the first collection of optical fiber output ends 206, the second collection of optical fiber output ends 226, and the third collection of optical fiber input ends 242, may be fixed, individually or collectively, into one or more fixtures (not shown), in desired first pattern 208, desired second pattern 228, and desired third pattern 244. For instance, in one embodiment of the invention, the first pattern 208, the second pattern 228, and the third pattern 244 can be chosen such that the first collection of optical fiber output ends 206 and the second collection of optical fiber output ends 226 are surrounded by a third collection of optical fiber input ends 242. It is likely that in such an embodiment a collection efficiency of backscattered light (the third light flux 240) from the surface 205 is enhanced, which in turn results in an improved signal-to-noise ratio.

It may be evident that the ultrasonic generation system 202 including the first collection of optical fibers 214, and the ultrasonic detection system 224 including the second collection of optical fibers 230 and the third collection of optical fibers 246, may be combined into a single collection of optical fibers. It may be evident that such an "integrated" system would allow for levels of compaction that are enhanced over currently available ultrasonic systems. In-situ applications as discussed herein may benefit from having such compact laser ultrasonic systems.

Figure 4:
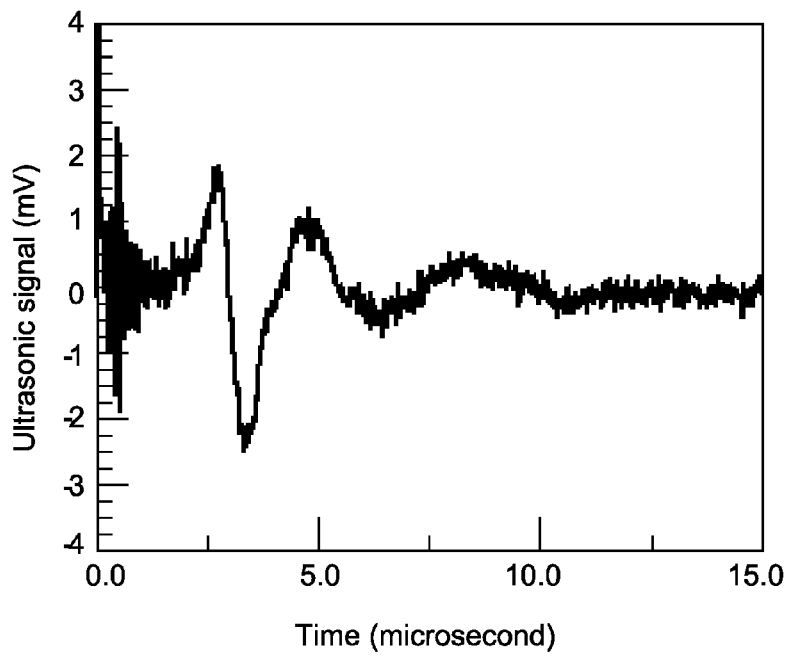
FIG. 4 is a typical experimentally measured time evolution of an ultrasonic signal on a surface of a ceramic coating deposited on a metallic substrate, in accordance with an embodiment of the invention.

In FIG. 4 is shown a typical experimentally measured time evolution 400 of an ultrasonic signal on a surface of a ceramic coating deposited on a metallic substrate corresponding to ultrasonic waves of type 203 that were produced in ablation mode. The ultrasonic signal was recorded via an ultrasound detection system 224 when the first pattern 208 is substantially a circle, the second pattern is substantially a point, and the third pattern is substantially a circle. For the ultrasonic signal shown in FIG. 3, the first light flux has an energy content of approximately 2 millijoules and was pulsed every approximately 10 nanoseconds, and the first collection of optical fiber output ends was placed at a distance of approximately 4 millimeters from the surface of the sample.

A collection efficiency of the ultrasonic detection system 224 is dependent upon the portion of the third light flux 240 that the third collection of optical fiber input ends 242 are able to collect. The collection efficiency is a function of several potentially inter-related factors such as, the individually independent numerical aperture of the individual optical fibers 222 corresponding to the first collection of optical fiber output ends 206, the individually independent numerical aperture of the individual optical fibers 236 corresponding to the second collection of optical fiber output ends 226, and the individually independent numerical aperture of the individual optical fibers 252 corresponding to the third collection of optical fiber input ends 242. To this end, in one embodiment of the invention, the numerical aperture of optical fibers 222 and 236 corresponding to the ultrasonic generation system 202 may be chosen to be smaller than the numerical aperture of the optical fibers 252 corresponding to the ultrasonic detection system 224. In one embodiment of the invention, the optical collection efficiency of the ultrasonic detection system is 224 between a range from about 0.5% to about 20% measured on a typical ceramic coating. It accordance with one embodiment of the invention, the collection efficiency is a function of the type of sample. For instance, other factors being held substantially constant, a collection efficiency for a polished aluminum sample is likely enhanced over a collection efficiency for a ceramic sample.

In one embodiment of the invention, an enhanced signal to noise ratio of signal may be obtainable by including at least one optical lens 254 within the laser ultrasonic device 200. In the embodiment shown in FIG. 2, the at least one optical lens 254 is shown as "localized" at a particular location within the laser ultrasonic device 200. However, it is to be clearly understood that the at least one optical lens 254 can be distributed across different locations within the laser ultrasonic device 200, and also within the medium 212. In one embodiment of the invention, other factors being constant, an obtainable signal-to-noise may be a function of the choice of the first pattern 208, and/or second pattern 228, and/or third pattern 244. For instance, it is likely that acoustically matched combinations of the first pattern 208, the second pattern 228, and third pattern 244 might result in enhanced levels of signal-to-noise ratio. One may obtain acoustically matched combinations when, for example, the first pattern 208, the second pattern 228, and third pattern 244, are all similar, for instance when each of these patterns is a line, or a point, or a circle.

In one embodiment of the invention, the signal to noise ratio of the ultrasonic detection system may be a function of a collection efficiency of the ultrasonic detection system 224.

The collection efficiency of the ultrasonic detection system 224 in turn is a function of a distance between the laser ultrasonic device 200 and the sample 204. In accordance with one embodiment of the invention, a distance 256 between an output end 258 of the ultrasonic generation system 202 and the sample 204 lies within a range from about 0.01 millimeters to about 20 millimeters. In accordance with one embodiment of the invention, a distance 257 or a distance 259 between an output end 258 of the ultrasonic detection system 224 and the sample 204 lies within a range from about 0.5 millimeters to about 5 millimeters.

Figure 5:
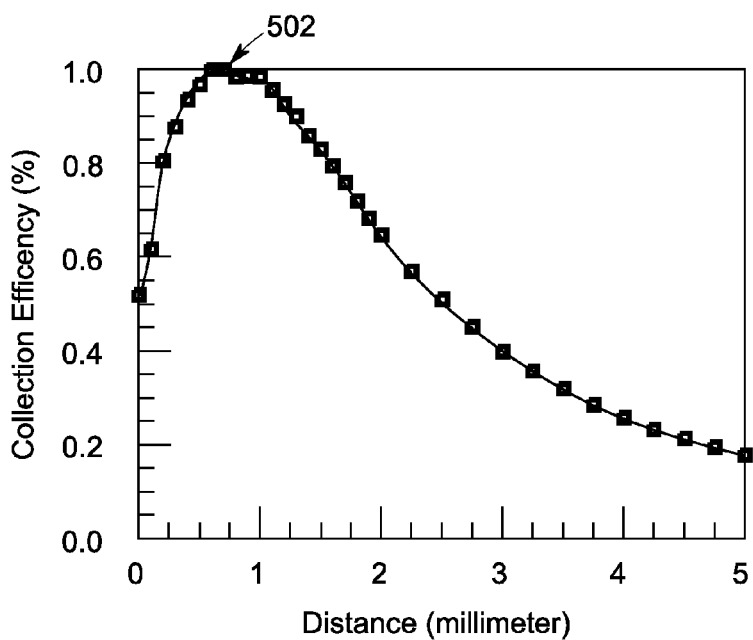
FIG. 5 is a typical experimentally measured variation of collection efficiency of an ultrasonic detection system as a function of a distance between a laser ultrasonic device and a sample, in accordance with one embodiment of the invention.

In FIG. 5 is shown a typical experimentally measured variation 500 of collection efficiency, of ultrasonic signal produced via ablation mode, as a function of distance between the laser ultrasonic device 200 and sample 204, when the first pattern 208 is substantially a circle, the second pattern is substantially a point, and the third pattern is substantially a circle. It may be evident that the collection efficiency has a peak value 502 of approximately 1.2% at a distance of approximately 0.8 millimeters between the laser ultrasonic device 200 and sample 204. Furthermore, it may be noted that providing one or more optical lenses between the sample and optical fiber input or output ends may result in an enhancement of an optical performance of the laser ultrasonic system. It is remarked that the laser ultrasonic systems constructed according to embodiments of the present invention, even when they do not include a system of lenses, provide for enhanced levels of collection efficiency over currently available laser ultrasonic systems.

Figure 6:
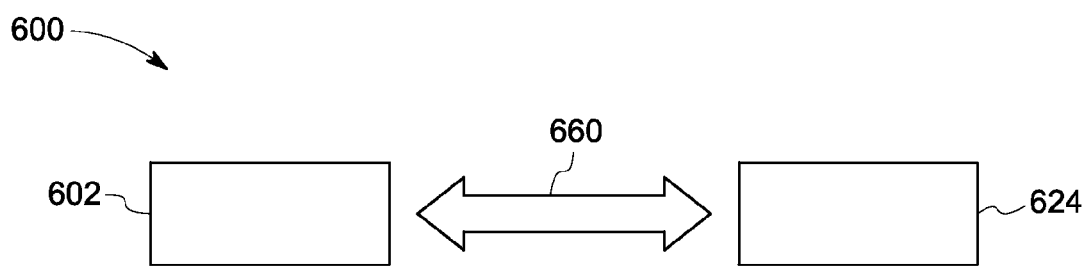
FIG. 6 is a schematic representation of a laser ultrasonic device, in accordance with one embodiment of the invention.

In accordance with one embodiment of the invention, a laser ultrasonic device 600 is disclosed and shown schematically in FIG. 6. The laser ultrasonic device 600 includes an ultrasonic generation system 602 capable of generating ultrasonic waves (not shown) on a surface of a sample (not shown). The ultrasonic generation system 602 includes a first collection of optical fiber output ends (not shown) arranged in a first pattern (not shown). The laser ultrasonic device 600 further includes an ultrasonic detection system 624 capable of detecting ultrasonic waves (not shown) on the surface (not shown) of a sample (not shown), so that the ultrasonic generation system 602 and ultrasonic detection system 624 are capable of communication 660 with each other. The ultrasonic detection system 624 includes a second collection of optical fiber output ends (not shown) arranged in a second pattern (not shown), and a third collection of optical fiber input ends (not shown) arranged in a third pattern (not shown). In one embodiment of the invention, the laser ultrasonic generation system 602 is substantially of the same type as the laser ultrasonic generation system 202. In one embodiment of the invention, the laser ultrasonic detection system 624 is substantially of the same type as the laser ultrasonic generation system 224.

Figure 7:
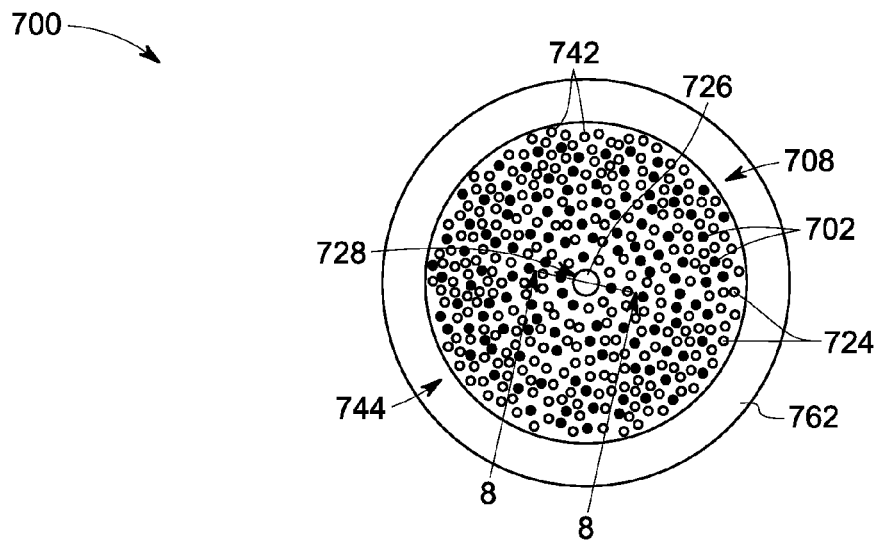
FIG. 7 is a cross-sectional view of a laser ultrasonic device in accordance with one embodiment of the invention.
Figure 8:
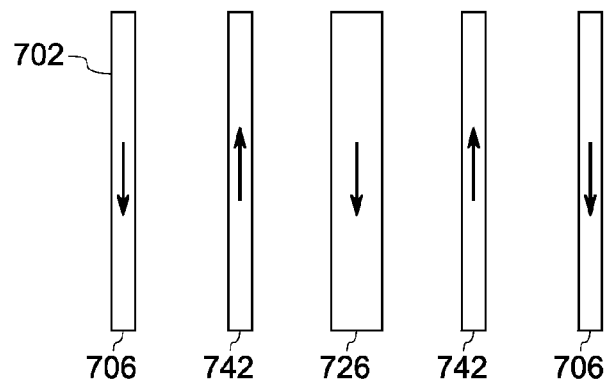
FIG. 8 is a schematic side view of the laser ultrasonic device of FIG. 7 in accordance with one embodiment of the invention.
Figure 8:
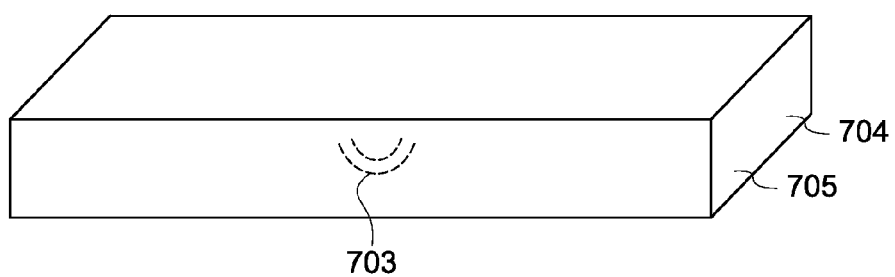

With specific reference to FIGS. 7 and 8, in accordance with one embodiment of the invention, a laser ultrasonic device 700 is disclosed and shown schematically in FIG. 7. The laser ultrasonic device 700 includes an ultrasonic generation system 702 capable of generating ultrasonic waves 703 within a bulk 705 of a sample 704. The ultrasonic generation system 702 includes a first collection of optical fiber output ends 706 arranged in a first pattern 708. The laser ultrasonic device 700 further includes an ultrasonic detection system 724 capable of detecting ultrasonic waves 703 within the bulk 705 of the sample 704. The ultrasonic detection system 724 includes a second collection of optical fiber output ends 726 arranged in a second pattern 728, and a third collection of optical fiber input ends 742 arranged in a third pattern 744. In one embodiment of the invention, the first pattern 708, the second pattern 728, and the third pattern 744 independently comprise an independent random pattern. In one embodiment, the first collection of optical fiber output ends 706, the second collection of optical fiber output ends 726, and the third collection of optical fiber input ends 742 are enclosed within a mechanical housing 762.

In accordance with one embodiment of the invention, in FIG. 8 is shown a side view along 8-8 (FIG. 7) of a first collection of optical fibers 714 corresponding to the first collection of optical fiber ends 706 is capable of guiding a first light flux (not shown) for delivery to a desired location (not indicated) within the bulk 705 of the sample 704. Said delivery of first light flux to location on the bulk 705 of sample 704, via the first collection of optical fiber output ends 706, likely results in a local thermoelastic heating of the location and its vicinity, as a result of which ultrasonic waves 703 are produced at location which acts as a generation center for ultrasonic waves 703 which propagate within the bulk 205 towards a surface of the sample 704. In one embodiment of the invention, a diameter of individual optical fibers corresponding to the first collection of optical fiber output ends 706 independently lies within a range from about 5 micrometers to about 1000 micrometers. In one embodiment of the invention, a diameter of individual optical fibers corresponding to the first collection of optical fiber output ends 706 independently lies within a range from about 50 micrometers to about 500 micrometers. Embodiments of the invention may also be capable of detecting lamb ultrasonic waves within a sample.

Figure 9:
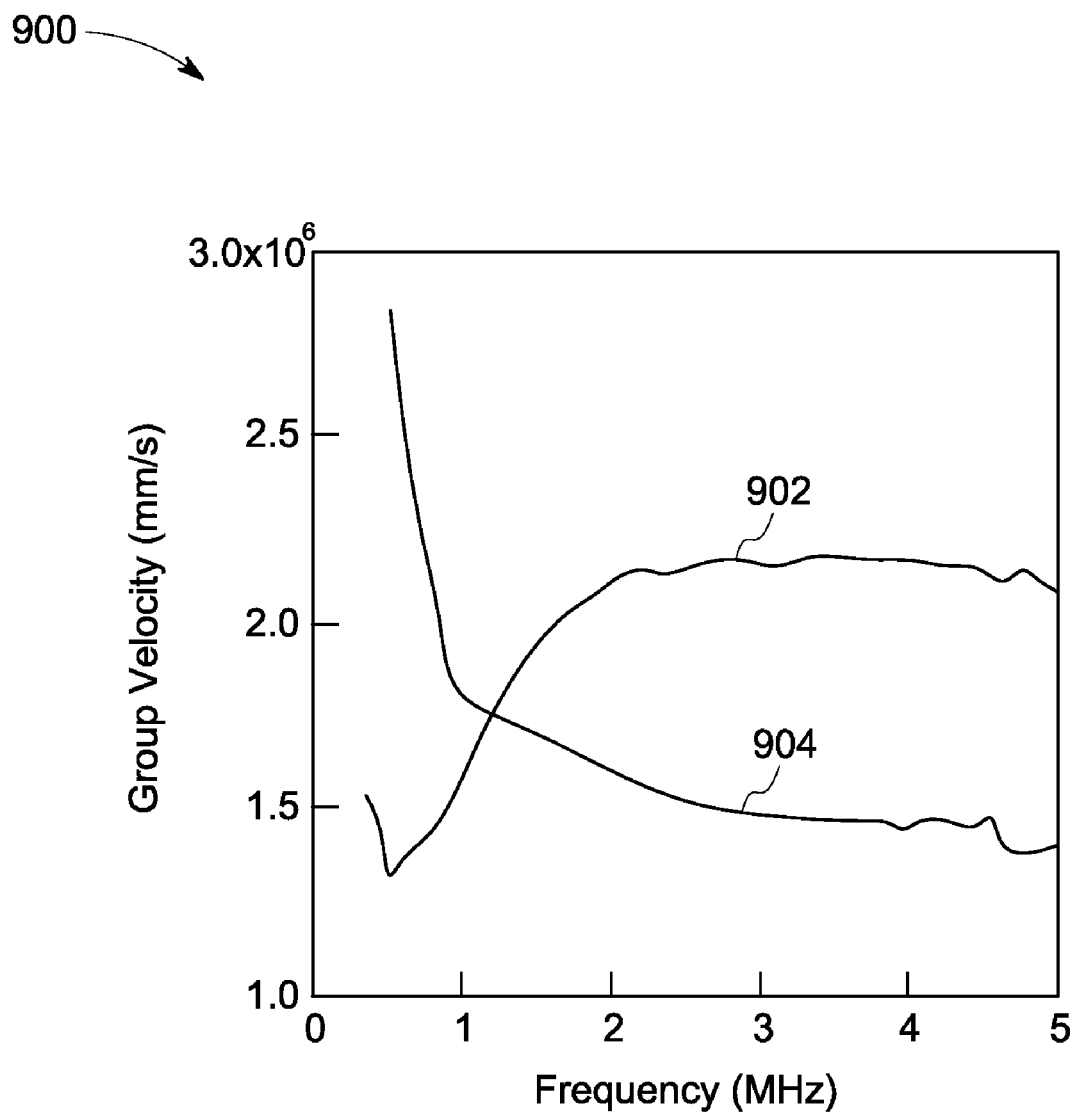
FIG. 9 is a graph showings results of measurements on a test system comprising a ceramic coating on a metallic substrate, in accordance with one embodiment of the invention.

The presently disclosed embodiments of the invention may be useful in a variety of applications. A non-limiting example of such applications includes measurements on a test system comprising a ceramic coating on a metallic substrate, wherein is measured an integrity of adhesion of the ceramic coating on the metallic substrate. FIG. 9 is a graph 900 showing the results of one such measurement performed in ablation mode. Plot 904 shows the frequency variation of a group velocity of ultrasonic waves within the test system. Plot 902 shows the frequency variation of a group velocity of ultrasonic waves within the same test system after performing an accelerated life time test on the test system that likely lead to a degradation of the coating and/or of an adhesion to the coating to the metallic substrate. It may be evident that, the frequency evolution of the ultrasonic waves for the test system before, and after performance of an accelerated lifetime test is distinguishable. Therefore a measurement of ultrasonic wave propagation properties, such as the ultrasonic wave group velocity, can be used to assess an integrity of adhesion of coatings on substrates.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A laser ultrasonic device, comprising:
   an ultrasonic generation system configured to generate ultrasonic waves on a surface of a sample, the ultrasonic generation system comprising:
   a first collection of optical fiber output ends arranged in a first pattern, wherein a first collection of optical fibers corresponding to the first collection of optical fiber output ends is configured to guide a first light flux.

2. The laser ultrasonic device of claim 1, wherein the first light flux comprises a first laser beam.

3. The laser ultrasonic device of claim 1, wherein the first light flux comprises electromagnetic energy having wavelength within a range from about 0.2 micrometers to about 15 micrometers.

4. The laser ultrasonic device of claim 1, wherein an intensity of the first light flux is sufficient for generation of ultrasonic waves in a thermoelastic mode or in an ablation mode.

5. The laser ultrasonic device of claim 1, wherein a cross-sectional area of the first collection of optical fibers corresponding to the first collection of optical fiber output ends is within a range from about 0.1 cm$^2$ to about 100 cm$^2$.

6. The laser ultrasonic device of claim 1, wherein the first pattern comprises a symmetrical pattern.

7. The laser ultrasonic device of claim 1, wherein the first pattern substantially is a point, a line, a circle, an arc, a square, a rectangle, or combinations thereof.

8. The laser ultrasonic device of claim 1, wherein a diameter of individual optical fibers corresponding to the first collection of optical fiber output ends independently lies within a range from about 5 micrometers to about 1000 micrometers.

9. The laser ultrasonic device of claim 1, wherein a numerical aperture of individual optical fibers corresponding to the first collection of optical fiber output ends independently lies within a range from about 0.05 to about 0.6.

10. The laser ultrasonic device of claim 1, further comprising at least one optical lens.

11. The laser ultrasonic device of claim 1, wherein a distance between an output of the ultrasonic generation system and the sample lies within a range from about 0.005 millimeters to about 20 millimeters.

12. The laser ultrasonic device of claim 1, further comprising an ultrasonic detection system configured to detect ultrasonic waves on the surface of the sample.

13. The laser ultrasonic device of claim 12, wherein the ultrasonic detection system comprises a second collection of optical fiber output ends arranged in a second pattern.

14. The laser ultrasonic device of claim 13, wherein a second collection of optical fibers corresponding to the second collection of optical fiber output ends is configured to guide a second light flux.

15. The laser ultrasonic device of claim 14, wherein the second light flux comprises a second laser beam.

16. The laser ultrasonic device of claim 14, wherein the second light flux comprises electromagnetic energy having wavelength within a range from about 0.2 micrometers to about 15 micrometers.

17. The laser ultrasonic device of claim 14, wherein a cross-sectional area of the second collection of optical fibers corresponding to the second collection of optical fiber output ends is within a range from about 0.1 cm$^2$ to about 10 cm$^2$.

18. The laser ultrasonic device of claim 14, wherein the second light flux is made to scatter off the surface of the sample to form a third light flux.

19. The laser ultrasonic device of claim 13, wherein the second pattern comprises a symmetrical pattern.

20. The laser ultrasonic device of claim 13, wherein the second pattern substantially is a point, a line, a circle, an arc, a square, a rectangle, or combinations thereof.

21. The laser ultrasonic device of claim 13, wherein a diameter of individual optical fibers corresponding to the second collection of optical fiber output ends independently lies within a range from about 2 micrometers to about 1000 micrometers.

22. The laser ultrasonic device of claim 13, wherein a numerical aperture of individual optical fibers corresponding to the second collection of optical fiber output ends independently lies within a range from about 0.05 to about 0.6.

23. The laser ultrasonic device of claim 12, wherein the ultrasonic detection system further comprises a third collection of optical fiber input ends arranged in a third pattern.

24. The laser ultrasonic device of claim 23, wherein the third collection of optical fiber input ends is configured to collect at least a portion of the third light flux.

25. The laser ultrasonic device of claim 23, wherein the third collection of optical fibers corresponding to the third collection of optical fiber input ends is configured to guide at least a portion of the third light flux.

26. The laser ultrasonic device of claim 23, wherein a cross-sectional area of a third collection of optical fibers corresponding individually to the third collection of optical fiber input ends independently lies within a range from about 0.1 cm$^2$ to about 5 cm$^2$.

27. The laser ultrasonic device of claim 23, wherein the third pattern comprises a symmetrical pattern.

28. The laser ultrasonic device of claim 23, wherein the third pattern is substantially a point, a line, a circle, an arc, a square, a rectangle, or any combinations thereof.

29. The laser ultrasonic device of claim 23, wherein a diameter of individual optical fibers corresponding to the third collection of optical fiber input ends independently lies within a range from about 2 micrometers to about 1000 micrometers.

30. The laser ultrasonic device of claim 23, wherein a numerical aperture of individual optical fibers corresponding to the third collection of optical fiber input ends independently lies within a range from about 0.05 to about 0.6.

31. A laser ultrasonic device, comprising:
an ultrasonic generation system configured to generate ultrasonic waves on a surface of a sample, the ultrasonic generation system comprising a first collection of optical fiber output ends arranged in a first pattern;
an ultrasonic detection system configured to detect ultrasonic waves on the surface of a sample, the ultrasonic detection system comprising:
a second collection of optical fiber output ends arranged in a second pattern; and
a third collection of optical fiber input ends arranged in a third pattern.

32. A laser ultrasonic device, comprising:
an ultrasonic generation system configured to generate ultrasonic waves within a bulk of a sample, the ultrasonic generation system comprising a first collection of optical fiber output ends arranged in a first pattern;
an ultrasonic detection system configured to detect ultrasonic waves within the bulk of the sample, the ultrasonic detection system comprising:
a second collection of optical fiber output ends arranged in a second pattern; and
a third collection of optical fiber input ends arranged in a third pattern.

33. The laser ultrasonic device of claim 32, wherein the first pattern comprises a random pattern.

34. The laser ultrasonic device of claim 32, wherein the second pattern comprises a random pattern.

35. The laser ultrasonic device of claim 32, wherein the third pattern comprises a random pattern.

36. The laser ultrasonic device of claim 32, wherein the first pattern, the second pattern, and the third pattern are substantially the same.

* * * * *